US008158575B2

(12) United States Patent  
Matthews et al.

(10) Patent No.: US 8,158,575 B2
(45) Date of Patent: Apr. 17, 2012

(54) AGENT FOR THE PREVENTION AND TREATMENT OF SEXUALLY TRANSMITTED DISEASES-I

(75) Inventors: Barry Ross Matthews, Olinda (AU); George Holan, Brighton (AU); Peter Karellas, Reservoir (AU); Scott Andrew Henderson, Rowville (AU); David Francis O'Keefe, Mount Waverley (AU)

(73) Assignee: Starpharma Pty., Ltd, Victoria (AU)

( * ) Notice: Subject to any disclaimer, the term of this patent is extended or adjusted under 35 U.S.C. 154(b) by 290 days.

(21) Appl. No.: 12/498,077

(22) Filed: Jul. 6, 2009

(65) Prior Publication Data

US 2009/0269298 A1    Oct. 29, 2009

Related U.S. Application Data

(62) Division of application No. 10/472,439, filed as application No. PCT/AU02/00407 on Mar. 28, 2002, now Pat. No. 7,589,056.

(30) Foreign Application Priority Data

Mar. 30, 2001   (AU) ........................................ PR4128

(51) Int. Cl.
*A01N 61/00*   (2006.01)
(52) U.S. Cl. ............ 514/1; 514/579; 514/646; 514/648; 514/706; 514/709; 977/754; 424/78.08
(58) Field of Classification Search .............. 514/1, 579; 424/78.08
See application file for complete search history.

(56) References Cited

U.S. PATENT DOCUMENTS

| 4,289,872 A | 9/1981 | Denkewalter et al. |
| 4,410,688 A | 10/1983 | Denkewalter et al. |
| 4,507,466 A | 3/1985 | Tomalia et al. |
| 4,558,120 A | 12/1985 | Tomalia et al. |
| 4,568,737 A | 2/1986 | Tomalia et al. |
| 4,587,329 A | 5/1986 | Tomalia et al. |
| 6,676,946 B2 | 1/2004 | Bay et al. |
| 7,030,037 B2 | 4/2006 | Doan et al. |
| 2003/0129158 A1 | 7/2003 | Matthews et al. |

FOREIGN PATENT DOCUMENTS

| WO | WO 95/34595 | 12/1995 |
| WO | WO 95/34595 A | 12/1995 |
| WO | WO 98/03573 A | 1/1998 |
| WO | WO 00/15239 A | 3/2000 |
| WO | WO 00/15240 A | 3/2000 |

OTHER PUBLICATIONS

N. Boarne et al., "Dendrimers, a New Class of Candidate Topical Microbicides with Activity against Herpes Simplex Virus Infection", Antimicrobial Agents and Chemotherapy, Sep. 2000, vol. 44, No. 9, pp. 2471-2474.
Myriam Witvrouw et al., "Polyanionic (i.e., Polysulfonate) Dendrimers Can Inhibit the Replication of Human Immunodeficiency Virus by Interfering with Both Virus Adsorption and Later Steps (Reverse Transcriptase/Integrase) in the Virus Replicate Cycle", Molecular Pharmacology, vol. 58, No. 5, 2000, pp. 1100-1108.
Prem Mohan et al., "Synthesis of Naphthalenesulfonic Acid Small Molecules as Selective Inhibitors of the DNA Polymerase and Ribonuclease H Activites of HIV-1 Reverse Transcriptase", J. Med. Chem. 1994, 37, pp. 2513-2519.
Dai et al., "Doping of conducting polymers by sulfonated fullerene derivatives and dendrimers", J. Phys. Chem. B 1998 102, 4049-4053.
Non-final office action U.S. Appl. No. 10/472,439 dated Jun. 3, 2008.
Notice of Allowance U.S. Appl. No. 10/472,439 dated Apr. 23, 2009.

*Primary Examiner* — Jake M. Vu
(74) *Attorney, Agent, or Firm* — Stephen A. Bent; Foley & Lardner LLP

(57) ABSTRACT

Use of a polylysine, polyamidoamine or polypropylenimine dendrimer having naphthyl disulphonate terminal groups as a topically applied agent in prophylaxis or treatment of sexually transmitted diseases.

5 Claims, No Drawings

AGENT FOR THE PREVENTION AND TREATMENT OF SEXUALLY TRANSMITTED DISEASES-I

CROSS-REFERENCE TO RELATED PATENT APPLICATIONS

This application is a Divisional of U.S. Ser. No. 10/472,439 filed Aug. 25, 2004, which is the U.S. National Phase of PCT/AU02/00407 filed Mar. 28, 2002, which claims priority from Australian Patent Application PR4128/01 filed Mar. 30, 2001, incorporated herein by reference in its entirety.

FIELD OF THE INVENTION

This invention relates to the prevention and treatment of sexually transmitted diseases, and in particular it relates to the use of a dendrimer having naphthyl disulphonate terminal groups as a topically applied agent in prophylaxis or therapeutic treatment of these diseases.

BACKGROUND OF THE INVENTION

The global incidence, morbidity, and mortality of sexually transmitted diseases (STDs) caused by HIV, HSV, and other viral and microbial pathogens is estimated at several hundred millions individuals worldwide. One approach for the control the transmission of STDs is the use of topically applied, female/male-controlled vaginal, or rectal microbicides that inactivate the relevant pathogens. Consequently, the development of new, safe, topical microbicides for intravaginal or intrarectal use for the prevention and treatment of STDs is an important target for novel drug development.

International Patent Application Nos. PCT/AU95/00350 (WO 95/34595) and PCT/AU99/00763 (WO 00/15240), the contents of which are incorporated herein by reference, disclose a new class of polyvalent agents—the dendrimers, highly branched macromolecules with a definite envelope of polyanionic or cationic surface groups, which have been shown to exhibit a range of antiviral and antimicrobial activity with minimal toxicity. Unlike small molecular structures of most antivirals, these dendrimers are a class of polyvalent, highly branched macromolecular compounds formed by iterative reaction sequences starting from an initial core molecule with successive layers or stages being added in successive "generations" to build up a three-dimensional, highly ordered polymeric compound. Dendrimers are characterised by the following features: i. an initiator core which may have one or more reactive sites and be point-like or of significant size so as to effect the final topology of the dendrimer; ii. layers of branched repeating units attached to the initiator core; iii. functional terminal groups (such as anionic- or cationic-containing moieties) attached to the surface of the dendrimer, optionally through linking groups.

These macromolecular compounds are synthesised from monomeric building blocks with multiple branches or tree-like structures, and the outside surface of the molecule carries a number of functional groups that lead to recognition by a biological receptor.

The preparation of dendrimers is well known, and is described by way of example in U.S. Pat. Nos. 4,289,872 and 4,410,688 (describing dendrimers based on layers of lysine units), as well as U.S. Pat. Nos. 4,507,466, 4,558,120, 4,568, 737 and 4,587,329 (describing dendrimers based on other units including polyamidoamine or PAMAM dendrimers).

In antiviral and antimicrobial testing, a subset of these dendrimer structures have unexpectedly shown exceptional activity against a broad spectrum of microorganisms associated with sexually transmitted diseases, that makes them agents of choice for the development of a vaginal or rectal microbicide for the prophylaxis and treatment of sexually transmitted diseases.

SUMMARY OF THE INVENTION

According to the present invention, there is provided a compound of the formula I, II, or III:

I

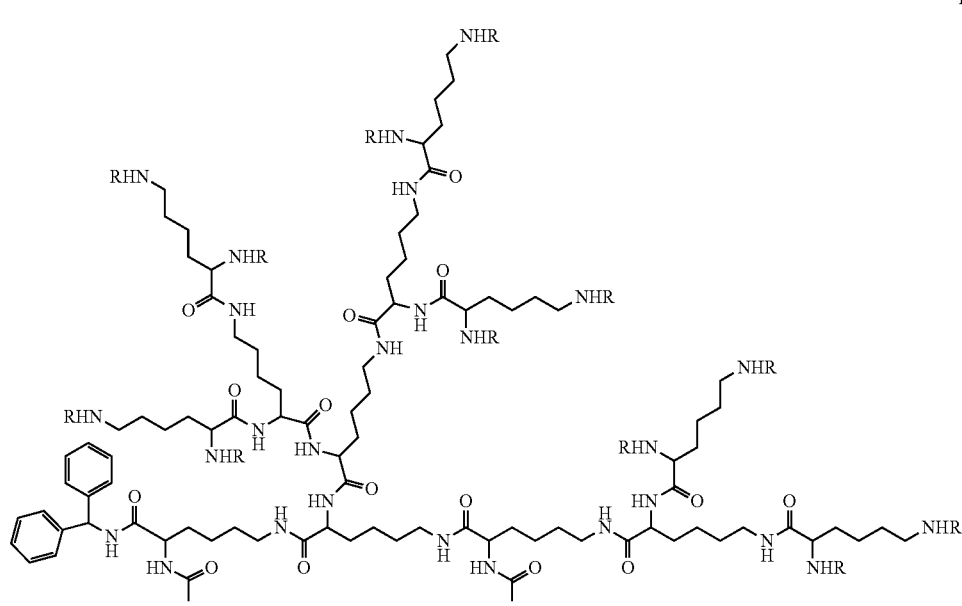

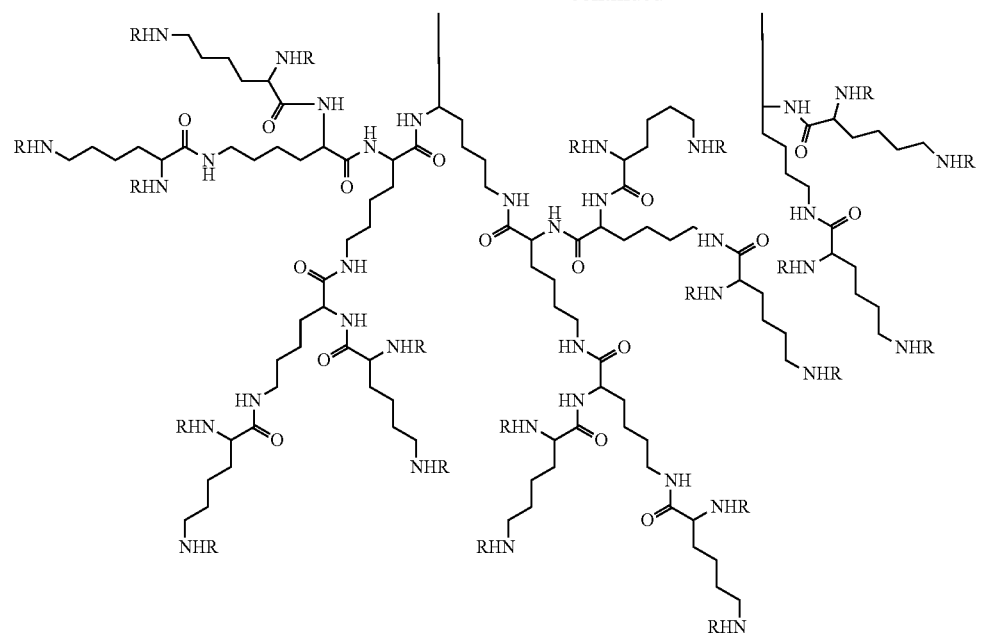
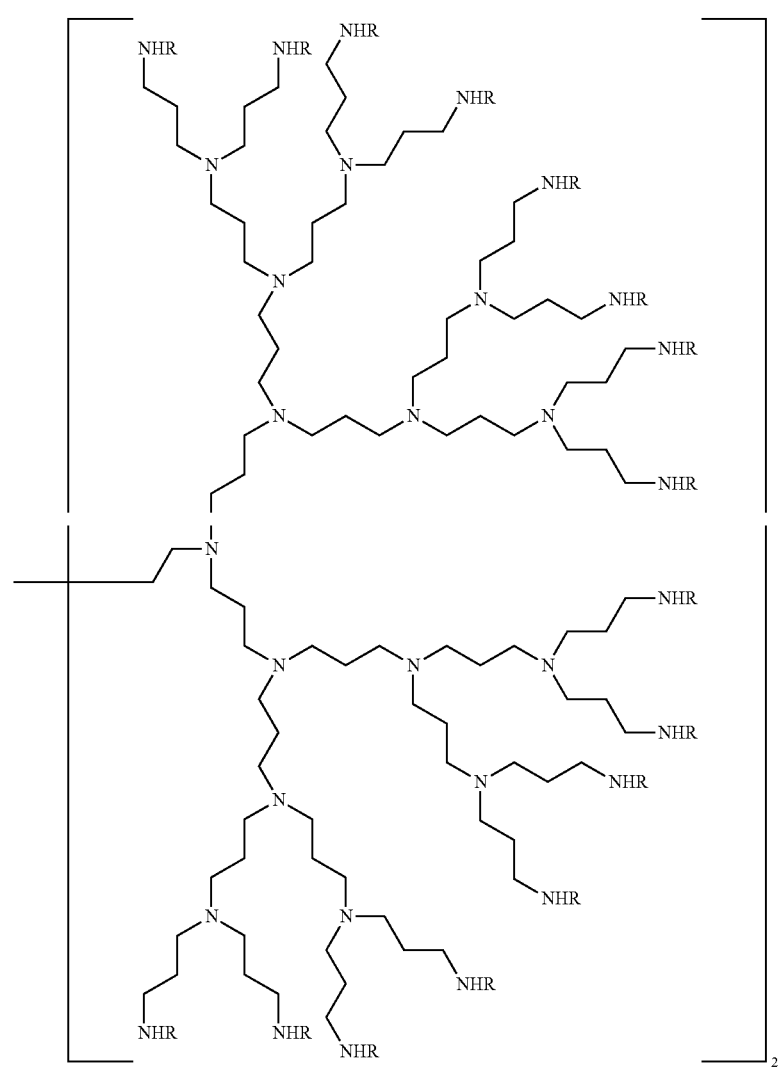
II

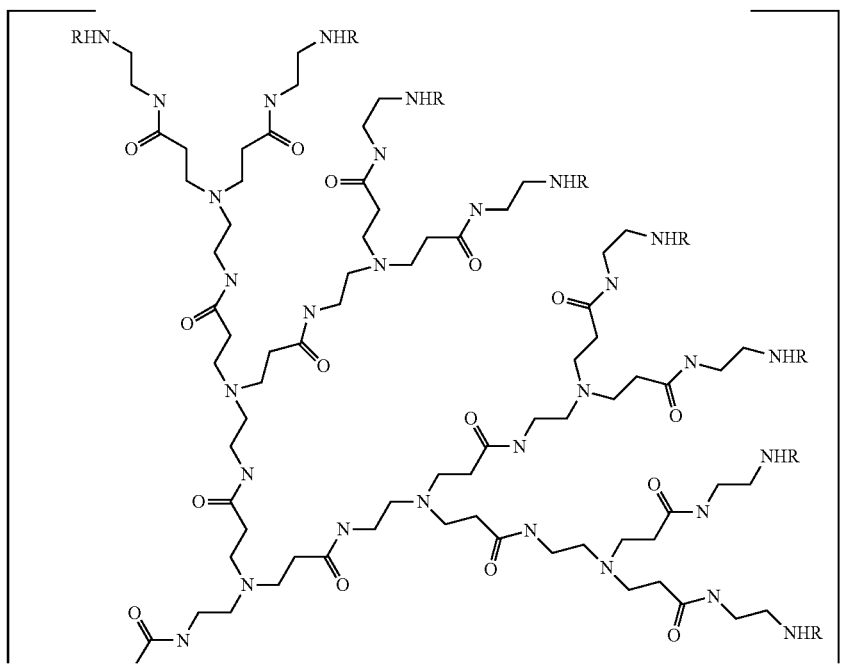
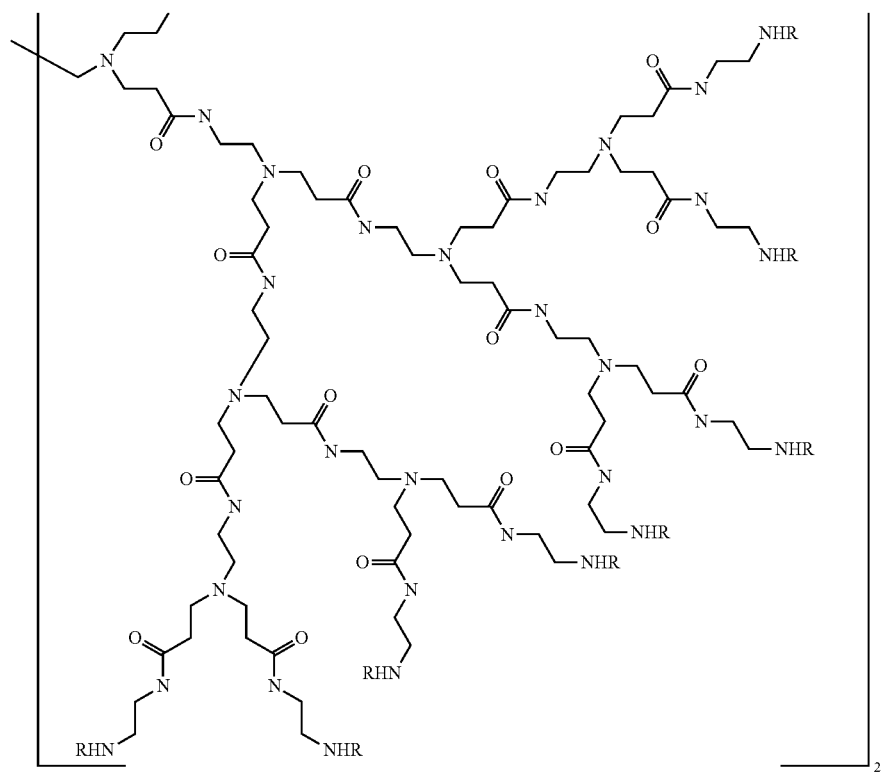

wherein R represents a group of the formula IV:

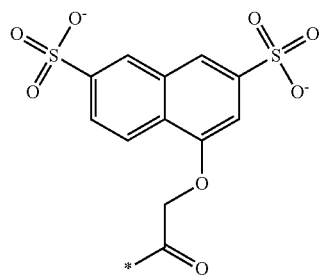

or a pharmaceutically acceptable salt thereof.

Suitable pharmaceutically acceptable base addition salts include, but are not limited to, metallic salts such as the aluminium, calcium, lithium, magnesium, potassium, sodium and zinc salts, as well as organic salts made from organic amines such as N,N'-dibenzylethylenediamine, chloroprocaine, diethanolamine, ethylenediamine, dicyclohexylamine, meglumine (N-methylglucamine) and procaine, quaternary amines such as choline, and sulphonium and phosphonium salts.

Particularly preferred compounds of the present invention are the compounds referred to herein as SPL-7013, SPL-7304 and SPL-7320 the structures of which consist of polylysine dendrimer, polyamidoamine (PAMAM) dendrimer, and polypropylenimine dendrimer scaffolds respectively with the active surface groups consisting of 32 naphthyl disulphonic acid groups as sodium salts. Each of the naphthyl-disulphonate functional surface groups is attached to the branched dendrimer scaffold with an amido-methyleneoxy linkage to the 32 terminal groups.

The present invention also provides a topical pharmaceutical composition for prophylactic or therapeutic treatment of sexually transmitted diseases in a human patient, which comprises a compound of the formula I, II, or III above or a pharmaceutically acceptable salt thereof, in association with at least one pharmaceutically acceptable, topical carrier or diluent.

In another aspect, the present invention also provides a method for the prophylactic or therapeutic treatment of sexually transmitted diseases in a human patient, which comprises topical administration to the patient of an effective amount of a compound of the formula I, II, or III above or a pharmaceutically acceptable salt thereof.

In yet another aspect, the invention provides use of a compound of the formula I, II, or III above or a pharmaceutically acceptable salt thereof in the manufacture of a medicament for topical administration in the prophylactic or therapeutic treatment of sexually transmitted diseases in a human patient.

DETAILED DESCRIPTION OF THE INVENTION

Compounds of the formula I, II, and III, and their pharmaceutically acceptable salts are novel compounds which have unexpectedly shown exceptional activity against a broad spectrum of pathogens associated with sexually transmitted diseases.

As described above, the compounds SPL-7013, SPL-7304, and SPL-7320 are preferred compounds of the present invention, and have been found to exhibit significant antiviral activity, particularly against viral and microbial vectors of the most common sexually transmitted diseases.

SPL-7013 exhibits a broad-spectrum antiviral activity with high efficacy and minimal cell or animal toxicity against vectors of several of the most important vaginally or rectally sexually transmitted diseases. High activity has been determined against genital Herpes virus-2 (HSV-2) both in in vitro cell tests and in vivo in an animal (mouse) model test and in vitro cell tests against Herpes virus-1 (HSV-1) and Human Immunodeficiency viruses (HIV-1, and HIV-2). It has also been shown to be active against the causative agent of genital warts, Human Papillomavirus (HPV), and against the bacterial vector of non-specific urethritis, *Chlamydia trachomatis*. In cell tests, SPL-7013 has also shown activity against viral strains of Herpes virus-2 resistant to currently used modified nucleoside based antiviral agents. In addition SPL-7304 and SPL-7320 show high activity against HSV-1, HSV-2, HIV-1, and HIV-2. Furthermore SPL-7013, SPL-7304, and SPL-7320 is active in CD4-dependant and CD4-independent HIV transmission assays, and is effective at preventing HIV-1 attachment and fusion. All compounds have been shown not to inhibit the growth of various species of beneficial *Lactobacillus*. In addition SPL-7013, SPL-7304, and SPL-7320 have been shown to be effective in the prevention of infection of human peripheral blood monocular cells (PBMCs) with either HIV-1 RoJo or SIV 89.6pd.

Accordingly, these compounds are useful in prophylaxis and therapeutic treatment of sexually transmitted diseases as topical microbicide agents intended for application to the vaginal or rectal mucosa to protect against sexually transmitted infections.

The present invention also provides a topical pharmaceutical composition for prophylactic or therapeutic treatment of sexually transmitted disease in a human patient, which comprises a compound of formula I, II, or III or salt thereof as described above, in association with at least one pharmaceutically acceptable, topical carrier or diluent.

The formulation of such compositions is well known to persons skilled in this field. Suitable pharmaceutically acceptable carriers and/or diluents include any and all conventional solvents, dispersion media, fillers, solid carriers, aqueous solutions, coatings, antibacterial and anti fungal agents, isotonic, and absorption enhancing or delaying agents, activity enhancing or delaying agents and the like. The use of such media and agents for pharmaceutically active substances is well known in the art, and it is described, by way of example, in *Remington's Pharmaceutical Sciences*, 18th Edition, Mack Publishing Company, Pennsylvania, USA. Except insofar as any conventional carrier and/or diluent is incompatible with the active ingredient, use thereof in the pharmaceutical compositions of the present invention is contemplated. Supplementary active ingredients including agents having antiviral or antimicrobial activity can also be incorporated into the compositions of this invention.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

As previously described, the present invention also provides a method for the prophylactic or therapeutic treatment of sexually transmitted diseases in a human patient by topical administration to the patient of an effective amount of a compounds of formula I, II or III or salt thereof as described above. In addition, the present invention provides the use of a compound of formula I, II, or III or salt thereof as described above in the manufacture of a medicament for topical administration in such prophylactic or therapeutic treatment of sexually transmitted diseases.

A variety of topical administration routes are available. The particular mode selected will depend, of course, upon the particular condition being treated and the dosage required for prophylactic or therapeutic efficacy. The methods of this invention, generally speaking, may be practiced using any mode of administration that is medically acceptable, meaning any mode that produces prophylactic or therapeutic levels of the active component of the invention without causing clinically unacceptable adverse effects. Such modes of administration include the vaginal, rectal, and trans-dermal routes. Suitable formulations for topical, particularly vaginal or rectal, administration include solutions, suspensions, gels, lotions and creams as well as discrete units such as suppositories and microencapsulated suspensions. Other delivery systems can include sustained release delivery systems which can provide for slow release of the active component of the invention, including sustained release gels, creams, suppositories, or capsules. Many types of sustained release delivery systems are available. These include, but are not limited to: (a) erosional systems in which the active component is contained within a matrix, and (b) diffusional systems in which the active component permeates at a controlled rate through a polymer.

The active component of the present invention is administered in prophylactically or therapeutically effective amounts. A prophylactically or therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgment. It will be understood by those of ordinary skill in the art; however, that a lower dose or tolerable dose may be administered for medical reasons, psychological reasons or for virtually any other reasons.

Generally, at intervals to be determined by the prophylaxis or treatment of pathogenic states, intra-vaginal or intra-rectal doses of active component will be from about 0.01 mg/kg per day to 1000 mg/kg per day. Small doses (0.01-1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day can be contemplated to achieve appropriate systemic levels of compounds.

In a particularly preferred aspect, the present invention provides the use of SPL-7013, SPL7304 or SPL7320 as a broad spectrum vaginal or rectal microbicide useful in the prevention and treatment of viral and microbial sexually transmitted diseases. SPL-7013, SPL7304 and SPL7320 are water soluble and can be used in solution, or formulated in a suitable vehicle in the form of gel, lotion, cream or suppository or microencapsulated suspension in aqueous or non-aqueous solvents, together with enhancers or delayers of its activity, agents for its enhanced or delayed absorption on topical application, or agents to enhance adhesion to vaginal/rectal epithelial or mucosal layers.

Throughout this specification and the claims which follow, unless the context requires otherwise, the word "comprise", or variations such as "comprises" or "comprising", will be understood to imply the inclusion of a stated step or steps or integer or group of integers but not the exclusion of any other step or steps or integer or group of integers.

Further features of the present invention will be apparent from the following Examples which are included by way of illustration, not limitation, of the invention.

EXAMPLE 1

A. Preparation of BHAlyslys$_2$lys$_4$lys$_8$lys$_{16}$ TFA$_{32}$

1. N,N'-Di-t-Boc-L-Lysine (DBL)

L-Lysine.HCl (1.83 kg; 10 mol) was dissolved in a solution of sodium hydroxide (880 g; 22 mol) in water (20 l) and the resulting solution diluted with t-butanol (15 l). Di-t-butyl dicarbonate (4.48 kg; 20.5 mol) was then added dropwise over 1 hour during which time the reaction mixture became milky and warm (30-35° C.). The mixture was left to stir overnight to give a clear solution. The solution was extracted with petroleum (40-60° C.) (2×10 l) and the organic phase extracted with sat. NaHCO$_3$ solution (3×4 l). The combined aqueous layers were cooled in an ice bath and acidified carefully to pH 2 with 1M KHSO$_4$ solution. The turbid mixture was then extracted with ether (4×16 l) and the combined organic layers washed with water (2×8 l), dried (MgSO$_4$) and concentrated with a bath temperature of <30° to give a quantitative yield of N,N'-di-t-Boc-L-Lysine as a very viscous oil.

2. N,N'-Di-t-Boc-L-Lysine 4-Nitrophenyl Ester (DBLONp)

A solution of dicyclohexylcarbodiimide (DCC) (2.06 kg; 10 mol) in ethyl acetate (5 l) was added dropwise to an ice-cold stirred solution of Di-t-Boc-L-lysine (DBL) (3.46 kg; 10 mol) and 4-nitrophenol (NpOH) (1.39 kg; 10 mol) in ethyl acetate (15 l) under nitrogen. After the addition was complete the mixture was allowed to warm to room temperature and stirred overnight. The resulting white suspension was then filtered and the filtrate concentrated to give a yellowish solid residue. The residue was recrystallised from ether to give N,N'-di-t-Boc-L-lysine 4-nitrophenyl ester as a white solid (yield ca. 60%). More of the product can later be isolated from the mother liquors.

3. BHAlys.2HCl

A solution of DCC (41.2 g; 0.2 mol) in dry dichloromethane (200 ml) was added to an ice-cold solution of DBL (69.2 g; 0.2 mol) and benzhydrylamine (BHA) (36.65 g; 0.2 mol) in dichloromethane (600 ml). The mixture was stirred at 0° for 30 minutes and then at room temperature for 3 hours. The resulting suspension was filtered and a tlc (pet.ether/EtOAc, 9:1) of the filtrate showed no starting material. The filtrate was washed with 5% HCl, water, sat. NaHCO$_3$ and water; then dried (MgSO$_4$) and concentrated to give a foam.

Trifluoroacetic acid (TFA) (400 ml) was added to a stirred solution of the foam in dry dichloromethane (200 ml) at room temperature. There was initially vigorous gas evolution which stopped after ca. 15 minutes; tlc (EtOAc) showed no starting material. The solution was stirred for an additional 2 hours and then concentrated to give a brownish oil. This oil was dissolved in dry acetonitrile (600 ml) and a saturated solution of HCl gas dissolved in absolute ethanol (ca. 360 ml) added with swirling. A white solid soon began to crystallise and the mixture was left to stand for 1 hour at room temperature to complete crystallisation. The mixture was filtered and the solid washed with dry acetonitrile, then dried to give BHAlys.2HCl as a white powder (yield ca. 80%).

4. BHAlyslys$_2$Boc$_4$

Triethylamine (39.5 ml; 0.283 mol) was added to a stirred solution of BHAlys.2HCl (54.4 g; 0.14 mol) in dry DMF (300 ml). A white suspension formed which was stirred for 15 minutes when DBLONp (262 g; 0.56 mol) was added. The mixture immediately became yellow and was stirred for 3 hours, maintaining the pH of the mixture at 8-9 by addition of triethylamine. The reaction mixture was then added slowly to a large volume of vigorously stirred water and the mixture stirred overnight. The precipitate was collected by filtration and washed with water (3×) and dried to give a yellowish solid. This solid was powdered and then washed successively with ether until the ether showed no yellow colour on treatment with aqueous NaOH. The remaining solid was dried to give BHAlyslys$_2$Boc$_4$ as a white powder (yield ca. 70%).

5. BHAlyslys$_2$lys$_4$ Boc$_8$

Trifluoroacetic acid (600 ml) was added to a solution of BHAlyslys$_2$Boc$_4$ (116 g; 0.12 mol) in dry dichloromethane (600 ml) and there was an immediate vigorous evolution of gas. The solution was stirred for 2 hours and the concentrated to give a viscous oil. This oil was dissolved in dry DMF (500 ml) and the pH of the solution adjusted to 8-9 with triethylamine. DBLONp (460 g; 0.99 mol) was then added and the yellow solution stirred for 2 days at room temperature with periodic pH adjustment with triethylamine to maintain the pH above 8. The reaction was then precipitated into water and worked up as described above to give BHAlyslys$_2$lys$_4$Boc$_8$ as a white powder (yield ca. 100%).

6. BHAlyslys$_2$lys$_4$lys$_8$Boc$_{16}$

Trifluoroacetic acid (1 l) was added to a solution of BHAlyslys$_2$lys$_4$Boc$_8$ (200 g; 0.106 mol) in dry dichloromethane (1 l) and there was an immediate vigorous evolution of gas. The solution was stirred for 2 hours and the concentrated to give a viscous oil. This oil was dissolved in dry DMF and the pH of the solution adjusted to 8-9 with triethylamine. DBLONp (782 g; 1.67 mol) was then added and the yellow solution stirred for 2 days at room temperature with periodic pH adjustment with triethylamine to maintain the pH above 8. The reaction was then precipitated into water and worked up as described above to give BHAlyslys$_2$lys$_4$lys$_8$Boc$_{16}$ as a white powder (yield ca. 100%).

7. BHAlyslys$_2$lys$_4$lys$_8$ lys$_{16}$ Boc$_{32}$

Trifluoroacetic acid (1.6 l) was added to a mixture of BHAlyslys$_2$lys$_4$lys$_8$Boc$_{16}$ (300 g; 0.081 mol) in dry dichloromethane (800 ml) and there was an immediate vigorous evolution of gas. The solution was stirred for 2 hours and the concentrated to give a viscous oil. This oil was dissolved in dry DMF (1.2 l) and the pH of the solution adjusted to 8-9 with triethylamine. DBLONp (1030 g; 2.21 mol) was then added and the yellow solution stirred for 2 days at room temperature with periodic pH adjustment with triethylamine to maintain the pH above 8. The reaction was then precipitated into water and worked up as described above to give BHAlyslys$_2$lys$_4$lys$_8$lys$_{16}$Boc$_{32}$ as a white powder (yield ca. 100%).

8. BHAlyslys$_2$lys$_4$lys$_8$lys$_{16}$ TFA$_{32}$

Trifluoroacetic acid (168 ml) was added in one portion to a suspension of the t-butyloxycarbonate (Boc) protected polylysine core BHAlyslys$_2$lys$_4$lys$_8$lys$_6$Boc$_{32}$ (20 g) in dichloromethane (350 ml) and the reaction was stirred for 14 hours at ambient temperature. The reaction mixture was concentrated in vacuo, dissolved in H$_2$O (200 ml) and freeze dried to give BHAlyslys$_2$lys$_4$lys$_8$lys$_{16}$TFA$_{32}$ (17.5 g, 83%) as an off-white solid.

B. Preparation of SPL 7013

(i) Disodium-[1-(oxymethylene-carboxyethyl)-3,6-naphthalene-disulphonate]

Disodium 1-hydroxy-3,6-naphthalene-disulphonate (100 g) was dissolved in dimethyl sulfoxide (250 ml) and diisopropylethylamine (60 ml) was added in one portion. Ethyl bromoacetate (38 ml) was added over a 30 min period and the reaction was stirred for 14 hours at ambient temperature with the exclusion of moisture. The reaction was slowly poured into ethyl acetate (2 L) to give an oily residue/gum. The supernatant was decanted and additional ethyl acetate (1.5 L) was added. Several triturations followed by washing with acetone of the residue gave disodium -[1-(oxymethylene-carboxyethyl)-3,6-naphthalene-disulphonate] (97 g, 78%) as a brown solid.

(ii) 1-(oxymethylene-carboxy)-3,6-naphthalene-disulphonic Acid

Aqueous NaOH (134 ml) was added in one portion to a solution of disodium-[1-(oxymethylene-carboxyethyl)-3,6-naphthalene-disulphonate] (97 g) in H$_2$O 500 ml. The reaction was stirred for 14 hours at ambient temperature and then passed through an IR120 (acid form) column. Freeze drying the collected fractions gave 1-(oxymethylene-carboxy)-3,6-naphthalene-disulphonic acid (67 g, 83%) as a brown solid.

(iii) BHAlyslys$_2$lys$_4$lys$_8$lys$_{16}$[NH—CO—CH$_2$)O-3,6-Naphthyl-(SO$_3$Na)$_2$]$_{32}$—SPL 7013

1-(oxymethylene-carboxy)-3,6-naphthalene-disulphonic acid (47.85 g) was dissolved in DMF (500 ml) and diisopropylethylamine (115 ml) was added in one portion. This solution was then added to a solution prepared by adding benzotriazole-1-yl-oxy-tris-pyrrolidino-phosphonium hexafluorophosphate (PyBOP; 72 g) in one portion to a solution of BHAlyslys$_2$lys$_4$lys$_8$lys$_{16}$TFA32 (15.95 g) in DMF (650 ml). DMF (100 ml) was used to rinse the dropping funnel. The reaction mixture was stirred for 14 hours at ambient temperature and then diluted with water (10 L). The solution was pumped through a 1 micron depth filter and across a Pall Filtron apparatus (Pall Gelman) containing a 10 kD membrane. The resulting solution was passed through an IR120 (sodium form) column, pumped through a 0.22 micron depth filter and freeze dried to give SPL-7013 as an off-white solid in a 75% yield. Retention time=15 min on an ODS-EC 15 cm×4.6 mm HPLC column at 30° C. with the detection wavelength set at 240 nm. The sample was eluted at a flow rate of 1 ml per minute using the gradient elution detailed below:

| Time mins | % A | % B |
| --- | --- | --- |
| 0 | 90 | 10 |
| 2 | 90 | 10 |
| 20 | 10 | 90 |
| 30 | 10 | 90 |
| 31 | 90 | 10 |

Where solvent A=0.015M TBAH in 0.01M NH$_4$OAc, (pH 7.0) and solvent B=0.015M TBAH in MeOH.

Mass spectral analysis of SPL7013 indicate a molecular weight of 16,580±2 Dalton. The expected average molecular weight expected for SPL7013, molecular formula, C$_{583}$H$_{577}$N$_{63}$Na$_{64}$O$_{287}$S$_{64}$ is 16581.53.

C. Preparation of SPL 7304

In a similar way SPL7304 was prepared by the PyBOP coupling of 1-(oxymethylene-carboxy)-3,6-naphthalene-disulphonic acid with polyamidoamine (PAMAM) dendrimer, generation 3 (Starburst®, Sigma-Aldrich Pty. Ltd., Australia).

D. Preparation of SPL 7320

In a similar way, SPL7320 was prepared by the PyBOP coupling of 1-(oxymethylene-carboxy)-3,6-naphthalene-disulphonic acid with polypropylenimine dotriacontaamine dendrimer, generation 4.0 (DAB-Am-32, Sigma-Aldrich Pty. Ltd., Australia).

EXAMPLE 2

Biological Activity of SPL 7013, SPL 7304, and SPL 7320

A. Activity Against Human Immunodeficiency Virus

The human immunodeficiency virus strains used were HIV-1 (IIIB)[1] and HIV-2 (ROD)[2]. Anti-retroviral activity and cytotoxicity measurements were carried out in parallel. They were based on the viability of MT-4 cells that had been infected with HIV and then exposed to various concentrations of the test compounds. After the MT-4 cells were allowed to proliferate for 5 days, the number of viable cells was quantified by a tetrazolium-based calorimetric 3-(4,5-dimethylthiazol-2-yl)-2,5-diphenyltetrazolium bromide (MTT) procedure in 96-well microtrays.[3]

In all of these assays, viral input (viral multiplicity of infection, MOI) was 0.01, or 100 times the 50% cell culture infective dose ($CCID_{50}$). The 50% antivirally inhibitory concentration ($EC_{50}$) was defined as the compound concentration required to protect 50% of the virus-infected cells against viral cytopathicity. The 50% cytotoxic concentration ($CC_{50}$) was defined as the compound concentration required to reduce the viability of mock-infected cells by 50%. The > symbol is used to indicate the highest concentration at which the compounds were tested and still found non-cytotoxic. Average $EC_{50}$ and $CC_{50}$ values for several separate experiments are presented as defined above. As a rule, the individual values did not deviate by more than 2-fold up or down from the $EC_{50}$ and $CC_{50}$ values. SI is the antiviral selectivity index $CC_{50}/EC_{50}$.

TABLE

HIV Activity

| Compound | Strain | EC50 µg/ml | EC90 µg/ml | CC50 µg/ml | SI |
|---|---|---|---|---|---|
| SPL-7013 | IIIB | 0.45 | 0.954 | >125 | >280 |
| | ROD | 3.26 | 4.86 | >50 | >17 |
| SPL-7304 | IIIB | 0.15 | | >88 | >652 |
| | ROD | 0.8 | | >50 | >63 |
| SPL-7320 | IIIB | 0.164 | | >88 | >537 |
| | ROD | 1.153 | | >50 | >47 |

IIIB = HIV-1 ROD = HIV-2
$EC_{90}$ = Effective concentration to reduce viral plaque 90%.

(i) Methods for the CD4-Dependent and CD4-Independent HIV Transmission Inhibition Assays, HIV Attachment and Fusion, and Inhibition of *Lactobacillus* sp. Growth.

Cells and Viruses:

HIV-1$_{IIIB}$, and the, HeLa CD4 LTR □-gal, GHOST X4/R5, and HL2/3 cell lines were obtained from the NIH AIDS Research and Reference Reagent Program (Bethesda, Md.), and maintained as recommended. ME180 cells were obtained from the American Type Culture Collection (Manassas, Va.).

Test Material Handling and Storage:

Compounds are typically solubilized in 100% DMSO and stored at −80° C. until tested, unless alternative solvents and storage conditions are specified by the sponsor. Frozen stocks are thawed at room temperature, pre-warmed for 15 min at 37° C. and vortexed prior to preparation of working solutions in tissue culture medium. During all stages of compound dilution and handling, compounds are protected from incidental light by opaque coverings and by storage and dilution in opaque or amber-colored tissue culture plastics. Additionally, incidental room and laminar flow tissue culture hoods light exposure is controlled by reducing total fluorescent lighting in the laboratory by 50%. The final DMSO concentration is 0.25% at the highest test concentration.

CD4-Independent HIV Transmission Inhibition Assay:

ME180 cells, a CD4 negative, X4 positive cervical epithelial cell line is maintained in RPMI 1640 supplemented with 10% fetal bovine serum, glutamine and antibiotics. Twenty-four h prior to the assay ME180 cells are trypsonized, washed and seeded in 96-well flat bottom microtiter plates at a density of $2 \times 10^3$ cells per well. On the day of the assay, H9 cells chronically infected with the SK1 clinical isolate of HIV-1 (H9-SK1) are treated with freshly made mitomycin C (200 µg/ml) for 60 minutes at 37° C. This concentration of mitomycin C is sufficient to result in cell death, but allows virus transmission to occur. After mitomycin C treatment the H9-SK1 cells are washed three times with tissue culture medium. Test compounds are added to the ME180 monolayer followed by $2 \times 10^4$ H9-SK1 cells. The ME180 cells are co-cultured with H9-SK-1 cells and test material for 4 h, and the H9-SK1 cells are removed by washing the ME180 monolayer three times with PBS. At 24 and 48 h post assay initiation the wells are again washed three times with PBS to ensure removal of the H9-SK1 cells, and culture continued in test material free media. At six days post-co-cultivation, supernatants are collected and evaluated for p24 antigen expression by ELISA. Cell viability is assessed by XTT dye reduction. Compounds which are judged as active in the first test are retested with or without the addition of mucin. Testing in the presence of mucin is carried out by addition of 200 □g/ml of porcine mucin (Sigma Chemical Co., St Louis, Mo.) to the transmission reactions. Transmission intervals and washing without replacement of mucin or compound are carried as described above. All determinations are performed in triplicate with serial ½ $Log_{10}$ dilution of the test materials.

CD4-Dependent HIV Transmission Inhibition Assay:

The CD4-independent HIV transmission inhibition assay is carried out essentially as described for the CD4-independent transmission assay except for the use of the CD4 positive GHOST(3) X4/R5 cell line. This cell line is derived from the HOS (human osteosarcoma) cell line that is negative for HIV coreceptor and CD4 expression. The cell line is engineered to express T4 (CD4), R5 and X4 via non-selectable retroviral vectors and an HIV-2 LTR hGFP construct with a hygromycin selectable marker. The cell lines are handled and cultured as described above for the CD4-independent HIV inhibition assay, with the exception that $2.5 \times 10^4$ GHOST(3) X4/R5 and $5 \times 10^2$ mitomycin C treated H9/SK-1 cells are used in the assay. Addition of compounds, mitomycin C treatment and post-transmission washing to remove the H9/SK-1 cells are performed as described above to allow comparability of the two antiviral assays. Virus replication is assessed at 24 h post infection, following 3 washes, by measurement of cell-associated p24 by ELISA to ensure a single round of infection in the presence of CD4. Compound toxicity and cell viability are assessed by XTT dye reduction. Compounds which are judged as active in the first test are retested with or without the addition of mucin. Testing in the presence of mucin is carried out by addition of 200 µg/ml of porcine mucin (Sigma Chemical Co., St Louis, Mo.) in tissue culture medium to the transmission reactions. Transmission intervals and washing without replacement of mucin or compound are carried as described above. All determinations are performed in triplicate with serial ½ $Log_{10}$ dilution of the test materials.

Lactobacillus Assay:

Lactobacillus crispatus and Lactobacillus jensenii were obtained from the American Type Tissue Culture Collection and grown in Lactobacilli MRS broth (Difco, Fisher Scientific, Pittsburgh, Pa.). This medium allows efficient growth of the Lactobacilli under anaerobic conditions. Bacillus stocks are produced and frozen in 15% glycerol at –80° C. for use in the sensitivity assay. To assess the effect of compounds on L. crispatus and L. jensenii growth, 10 ml of MRS media is inoculated with a stab from the glycerol bacterial stock. The culture is placed in a Gas Pak $CO_2$ bag and incubated for 24 h at 37° C. The next day the lactobacillus cultures are diluted to an OD of 0.06 at a wavelength of 670 nm. Compounds are diluted and placed into a 96 well flat bottomed plate and the Lactobacillus sp. added. Commercially available Penicillin/Streptomycin solution at a high test concentration of 1.25 U/ml and 1.25 µg/ml, respectively, are used as the positive control. The plates are again incubated for 24 h at 37° C. in a Gas Pak $CO_2$ bag and bacterial growth determined by measurement of optical density at 490 nm in a molecular devices plate reader. All determinations are performed with 6½ log dilutions from a high test concentration in triplicate.

Virus Attachment Assay:

This assay is designed to detect compounds that interact with the cell and block virus attachment, and/or compounds which interact with the forming attachment/fusion complex. The attachment assay is performed with HeLa CD4 LTR □-gal cells. HeLa CD4 LTR □-gal cells are routinely cultured with the required selection antibiotics. Twenty-four h prior to initiation of the assay the cells are trypsinized, counted and $1\times10^4$ cells placed in a 0.2 cm well in media without selection antibiotics. At 24 h media is removed and compound in media placed on the cells and incubated for 15 min at 37° C. A known titer of the IIIB strain of HIV is then added to the wells and the incubation continued for 1 h. At the end of the incubation the wells are washed 3 times with media and the culture continued for 40 to 48 h. At termination of the assay, media is removed and □-galactosidase enzyme expression determined by chemiluminescence per manufacturers instructions (Tropix Gal-screen™, Bedford Mass.) by a single step chemiluminescent method using a single solution to lyse the cells and detect □-galactosidase enzyme activity. Compound toxicity is monitored on a sister plate by XTT dye reduction. All determinations are performed in triplicate with serial ½ $Log_{10}$ dilution of the test materials. The virus adsorption interval of 1 h is sufficiently short that AZT, which requires phosphorylation to its active tri-phosphate form (AZT-TTP), is not active in this assay.

Fusion Assay:

The fusion assay assesses the ability of compounds to block cell-to-cell fusion mediated by HIV-1 Env and CD4 expressed on separate cells. This assay is sensitive to inhibitors of both the gp120/CD4 interaction and inhibitors of the X4 coreceptor. First, $5\times10^3$ HeLa CD4 LTR □-gal cells are placed in microtiter wells and incubated overnight. The following day the media is removed and the HeLa CD4 LTR □-gal cells are incubated for 1 h at 37° C. in fresh media with test compound. Following the incubation $5\times10^3$ HL2/3 cells are added and the incubation continued for 40 to 48 h. At 40 to 48 h □-galactosidase enzyme expression is detected by chemiluminescence (Tropix Gal-screen™, Tropix, Bedford, Mass.). Compound toxicity is monitored on a sister plate using XTT dye reduction. All determinations are performed in triplicate with serial ½ $Log_{10}$ dilution of the test materials.

P24 Antigen ELISA:

ELISA kits are purchased from Coulter Electronics, and detection of supernate or cell-associated p24 antigen is performed according to the manufacturer's instructions. For cell-associated p24, cell lysates are produced by lysis of the well contents in 25 to 50 µl of Coulter supplied virus lysis buffer, and assayed following 1 round of freeze/thaw. All p24 determinations are performed following serial dilution of the samples to ensure absorbances in the linear range of the standard p24 antigen curve. The standard curve is produced using manufacturer supplied standards and instructions. Data are obtained by spectrophotometric analysis at 450 nm using a Molecular Devices Vmax plate reader. Final concentrations are calculated from the optical density values using the Molecular Devices Soft Max software package and expressed in pg/ml p24 antigen.

XTT Staining for Cell Viability and Compound Cyotoxicity:

$TC_{50}$ values for the test materials are derived by measuring the reduction of the tetrazolium dye XTT (2,3-bis(2-methoxy-4-nitro-5-sulfophenyl)-5-[(phenylamino)carbonyl]-2H-tetrazolium hydroxide) in replicate microtiter plates containing cell and compound without virus. XTT is metabolized by the mitochondrial enzyme NADPH oxidase in metabolically active cells to a soluble formazan product, allowing the rapid quantitative analysis cell viability and compound cytotoxicity. XTT solution is prepared daily as a stock of 1 mg/mL in PBS. Phenazine methosulfate (PMS) solution is prepared at 15 mg/mL in PBS and stored in the dark at –20° C. XTT/PMS stock is prepared immediately before use by diluting the PMS 1:100 into PBS and adding 40 µl per mL of XTT solution. Fifty microliters of XTT/PMS are added to each well of the plate and the plate incubated for 4 h at 37° C. The 4 h incubation has been empirically determined to be within the linear response range for MTS dye reduction with the indicated numbers of cells for each assay. Adhesive plate sealers are used in place of the lids, the sealed plate is inverted several times to mix the soluble formazan product and the plate is read at 450 nm with a Molecular Devices Vmax 96 well plate format spectrophotometer.

Data Analysis

Dextran sulfate (positive) and dextran (negative) are used as controls for the CD4-dependent and CD4-independent HIV transmission inhibition assays. The sulfonic acid dye Chicago Sky Blue is used as a positive control for the attachment and fusion assays[4]. Commercially available Penicillin (10,000 U/ml) Streptomycin (10.0 mg/ml) solution is used as a positive control for the Lactobacillus sensitivity assay. For each compound, where appropriate, an $IC_{50}$ (concentration inhibiting virus replication or transmission by 50%), $ID_{50}$ (concentration inhibiting 50% growth of Lactobacilli) $TC_{50}$ (concentration resulting in a 50% reduction in cell viability) and a therapeutic index (TI: $TC_{50}/IC_{50}$ or $ID_{50}$) is calculated by linear regression.

RESULTS OF THE CD4-DEPENDENT AND CD4-INDEPENDENT TRANSMISSION ASSAYS

| Compound | Exp. # | Mucin | CD4-Independent Transmission Assay ($\mu$g/ml) | | | CD4-Dependent Transmission Assay ($\mu$g/ml) | | |
|---|---|---|---|---|---|---|---|---|
| | | | $IC_{50}$ | $TC_{50}$ | TI | $IC_{50}$ | $TC_{50}$ | TI |
| Dextran Sulfate | 1 | − | | | | 0.316 | >100 | >316 |
| | 2 | − | 1.1 | >50 | >46 | 0.158 | >50 | >316 |
| | 2 | + | 0.16 | >50 | >309 | 0.158 | >50 | >316 |
| Dextran | 1 | − | | | | >100 | >100 | — |
| | 2 | − | >100 | >100 | — | >100 | >100 | — |
| | 2 | + | >100 | >100 | — | >100 | >100 | — |
| SPL7013 | 1 | − | | | | 0.76 | >100 | >132 |
| | 2 | − | 28.5 | >100 | >3.5 | 0.39 | >100 | >256 |
| | 2 | + | 1.1 | >100 | >90.9 | 0.49 | >100 | >205 |
| SPL7304 | 1 | − | | | | <0.3 | >100 | >316 |
| | 2 | − | 5.0 | >100 | >20 | 0.89 | >10 | >112 |
| | 2 | + | 2.8 | >100 | >36 | 0.65 | >100 | >153 |
| SPL7320 | 1 | − | | | | <0.3 | >100 | >316 |
| | 2 | − | 0.8 | >100 | >125 | 0.68 | >100 | >147 |
| | 2 | + | 0.8 | >100 | >125 | 1.15 | >10 | >87 |

Results of the *Lactobacillus* sp. Testing

| Compound | Units | *L. crispatus* ($ID_{50}$) | *L jensenii* ($ID_{50}$) | Comments |
|---|---|---|---|---|
| Penicillin/Streptomycin | Dilution[1] | 1:150,00 | 1:180,000 | Control Compound |
| SPL7013 | $\mu$g/ml | >100 | >100 | |
| SPL7304 | $\mu$g/ml | >100 | >100 | |
| SPL7320 | $\mu$g/ml | >100 | >100 | |

[1] The starting concentrations of Penicillin and Streptomycin are 1.25 U/ml and 1.25 $\mu$g/ml, respectively.

Results of the Attachment and Fusion Inhibition Assays

| Compound | Attachment Assay ($\mu$g/ml s) | | | Fusion Assay ($\mu$g/ml) | | |
|---|---|---|---|---|---|---|
| | $IC_{50}$ | $TC_{50}$ | TI | $IC_{50}$ | $TC_{50}$ | TI |
| Chicago Sky Blue | 0.66 | >10 | >15 | 0.79 | >10 | >12 |
| | 0.09 | >10 | >111 | 0.62 | >10 | >16 |
| SPL7013 | 0.57 | >100 | >175 | 0.71 | >100 | >141 |
| SPL7304 | <0.32 | >100 | >312 | <0.32 | >100 | >312 |
| | 0.036 | >1 | >2778 | 0.56 | >1 | >178 |
| SPL7320 | <0.32 | >100 | >312 | 0.49 | >100 | >204 |
| | 0.049 | >1 | >2041 | | | |

(ii) Activity of SPL7013, SPL7304 and SP17320 Against HIV-1 RoJo and SIV 89.6pd

METHODS

Viruses

Human immunodeficiency virus type 1 (HIV-1) strain RoJo is a low passage pediatric isolate derived in the laboratories of Southern Research Institute (SRI). The SHIV89.6pd was obtained from Mark Lewis at SRI and stocks grown in human PBMCs for antiviral testing.

PBMC Isolation and Blasting:

Peripheral blood monocular cells (PBMCs) were obtained from normal hepatitis and HIV-1 negative donors by ficoll hypaque gradient separation. Briefly, anti-coagulated blood was diluted 1:1 with Dulbecco's phosphate buffered saline without $Ca^{++}$ and $Mg^{++}$ (PBS) and layered over 14 mL of Lymphocyte separation media in a 50 ml centrifuge tube. Tubes were then centrifuged for 30 minutes at 600×g. Banded PBLs were gently aspirated from the resulting interface and subsequently washed 2× with PBS by low speed centrifugation. The mononuclear cells were counted, viability determined by Trypan Blue dye exclusion and resuspended in RPMI 1640 medium supplemented with 15% FBS (heat inactivated), 2 mM L-glutamine, 100 U/mL penicillin, 100 $\mu$g/mL streptomycin, and 10 $\mu$g/mL gentamycin with 2 $\mu$g/mL phytohemagluttin (PHA) at $1\times10^6$ cells/mL. The cells were cultured for 48 to 72 h at 37° C., 5% $CO_2$. Following incubation, cells were collected by centrifugation, washed and resuspended in RPMI 1640 supplemented with 15% FBS (heat inactivated), 2 mM L-glutamine, 100 U/mL penicillin, 100 $\mu$g/mL streptomycin, and 10 $\mu$g/mL gentamycin with 20 U/mL recombinant IL-2 (R & D Systems, Minneapolis, Minn.). IL-2 was included in the culture medium to maintain the cell division initiated by the PHA mitogenic stimulation. The cells were cultured in IL-2 for 72 hours and then used for viral challenge.

PBMC Assay:

Human peripheral blood mononuclear cells from a minimum of 2 donors, that have been blasted with PHA and IL-2, were counted, viability determined by Trypan Blue dye exclusion and mixed in equal ratios. Pooled donors were used to minimize the variability observed between individual donors which results from quantitative and qualitative differences in HIV infection and overall response to the PHA and IL-2 of primary lymphocyte populations. The cells were resuspended at $1\times10^6$ cells/mL in RPMI 1640 without phenol red supplemented with 15% Fetal Bovine Serum (heat inactivated), 2 mM L-glutamine, 100 U/mL penicillin, 100 μg/mL streptomycin, 10 μg/mL gentamycin and IL-2 (20 U/mL, R&D Systems, Minneapolis, Minn.). Fifty microliters of cells were then distributed to the inner 60 wells of a 96 well round bottom microtiter culture plate in a standard format developed by the Infectious Disease Research department of Southern Research Institute. Each plate contains cell control wells (cells only), virus control wells (cells plus virus), and experimental wells (drug plus cells plus virus). Serially diluted compounds are added to the microtiter plate followed by the appropriate pre-titered strain of HIV-1 or SHIV-1. All samples were assayed in triplicate with a replicate plate without virus for the determination of compound toxicity. The final volume per well was 200 μL. The assay was incubated for 6 days in a humidified atmosphere at 37° C., 5% CO$_2$, after which supernatants were collected, for analysis of RT activity and sister plates analyzed for cell viability by MTS dye reduction. Wells were also examined microscopically and any abnormalities noted.

MTS Staining for Cell Viability:

At assay termination the assay plates were stained with the soluble tetrazolium-based dye MTS (CellTiter® Reagent Promega, Madison, Wis.) to determined cell viability and quantify compound toxicity. MTS is metabolized by the mitochondria enzymes of metabolically active cells to a soluble formazan product, allowing the rapid quantitative analysis of cell viability and compound cytotoxicity. This reagent is a single stable solution that does not require preparation before use. At termination of the PBMC assay 20 μL of MTS reagent was added per well, and the wells are incubated for 4 h at 37° C. T Adhesive plate sealers were used in place of the lids, the sealed plate was inverted several times to mix the soluble formazan product and the plate was read spectrophotometrically at 490 nm with a Molecular Devices Vmax plate reader.

Reverse Transcriptase Assay:

Reverse transcriptase activity was measured in cell-free supernatants. Tritiated thymidine triphosphate (NEN) (TTP) was resuspended in distilled H$_2$O at 5 Ci/mL. Poly rA and oligo dT were prepared as a stock solution which was kept at −20° C. The RT reaction buffer was prepared fresh on a daily basis and consists of 125 μL 1.0 M EGTA, 125 μL dH$_2$O, 110 μL 10% SDS, 50 μL 1.0 M Tris (pH 7.4), 50 μL 1.0 M DTT, and 40 μL 1.0 M MgCl$_2$. These three solutions were mixed together in a ratio of 2 parts TTP, 1 part poly rA:oligo dT, and 1 part reaction buffer. Ten microliters of this reaction mixture was placed in a round bottom microtiter plate and 15 μL of virus containing supernatant was added and mixed. The plate was incubated at 37° C. in a water bath with a solid support to prevent submersion of the plate and incubated for 60 minutes. Following reaction, the reaction volume was spotted onto pieces of DE81 paper, washed 5 times for 5 minutes each in a 5% sodium phosphate buffer, 2 times for 1 minute each in distilled water, 2 times for 1 minute each in 70% ethanol, and then dried. Opti-Fluor O was added to each sample and incorporated radioactivity was quantitated utilizing a Wallac 1450 Microbetaplus liquid scintillation counter.

Data Analysis:

IC$_{50}$ (50%, inhibition of virus replication), TC$_{50}$ (50% reduction in cell viability) and a therapeutic index (TI, IC$_{50}$/TC$_{50}$) are provided. AZT has been used as a relevant positive control compound for the individual assays.

The results of the antiviral evaluations performed are summarized in the following table:

Summary of the Antiviral Activity of Compounds in PBMCs

| Compound | HIV-1 RoJo Infected PBMCs (μg/ml) | | | SHIV 89.6pd Infected PBMCs (μg/ml) | | |
|---|---|---|---|---|---|---|
| | IC$_{50}$ | TC$_{50}$ | TI | IC$_{50}$ | TC$_{50}$ | TI |
| SPL7013 | 6.1 | >100 | >16 | 0.25 | >100 | >400 |
| SPL7304 | 13.2 | >100 | >7.6 | 0.92 | >100 | >109 |
| SPL7320 | 2.6 | >100 | >39 | 0.29 | >100 | >345 |
| AZT (μM) | 0.005 | >1 | >200 | 0.002 | >1 | >500 |

B. Activity Against Herpesviruses—HSV-1 and HSV-2

(i) Virus Plaque Reduction Assay

General Method

HSV standard strains G (HSV-2) and F (HSV-1) were used in the tests. Virus input for a 6-well plate was 100 pfu/well. HSV susceptible cell line, Vero cells, were used in the virus yield reduction assay. For cytotoxicity test, an epithelial cell line, Hela-229 cells, was employed.

The antiviral effects the compounds were determined by modified plaque reduction assay. Confluent cells were washed with PBS and subsequently infected with HSV (100 pfu/well) for 1 h at 37° C. and tilting every 10 min. After viral inoculum was removed, infected cells were washed with PBS and overlaid with 0.5% methylcellulose in culture medium (equal volume of 1% methylcellulose mixed with 2× culture medium). The cells were incubated at 37° C. for 2 days for HSV-2 infection and 3 days for HSV-1. When plaque size was adequate, the cells were fixed with 10% formalin for 10 min. The plaques were subsequently stained with 0.5% crystal violet for 10 min. The dye was removed by washing with tap water and left to dry in a fume hood. The plaques were then counted.

All data were generated from duplicate experiments. Mean plaque counts in test wells were compared with mean plaque counts in control wells.

EC$_{50}$'s (concentrations giving a 50% reduction in the plaque count of the inoculum) were calculated. Anti-viral activities and cytotoxicity measurements were carried out in parallel in the same strain of cells. The 50% cytotoxic concentration (CC$_{50}$) was defined as the compound concentration required to reduce the viability of mock-infected cells by 50%.

Pre-Infection Treatment Method

Culture medium was removed from confluent Vero cells in 6-well plate. and washed with 1 ml of PBS. 1 ml culture medium containing the compound at concentration of 0, 0.01, 0.03, 0.1, 0.3, 1, 3, 10, and 30 μg/ml was added to each well and incubated at 37° C. for 1 h. Following pre-incubation of the cells with dendrimer, the cells were then infected with 100 pfu/well of either HSV-1 or HSV-2. The infections were incubated at 37° C. for 1 h with tilting every 10 min. After the inoculum was removed, the infected cells were covered with 1.5 ml of 0.5% methylcellulose diluted with 2× culture medium for plaque assay.

Treatment of Infected Cells

Confluent Vero cells were washed with PBS. The cells were then infected with 100 pfu/well of either HSV-1 or -2 at 37° C. for 1 h. Following removal of viral inoculum, the infected cells were washed once with PBS and covered with 0.5% methylcellulose containing dendrimer at concentrations of 0, 0.03, 0.1, 0.3, 1, 3, 10, 30, and 100 μg/ml. The cells were incubated at 37° C. for 2 (HSV-2) or 3 (HSV-1) days for plaque assay.

Cytotoxicity of Dendrimer

Culture medium was removed from confluent Hela-229 cells in 24-well plates by pump. The cells were then washed once with 1 ml of PBS. 1 ml culture medium containing dendrimers at concentrations of 0, 100, 500, and 1000 μg/ml was added to each well. The cells were incubated at 37° C. incubator for 2 days. At end of incubation, the medium was removed and the cells washed with PBS. 500 μl of 0.01% neutral red (in PBS) was subsequently added to each well, and incubated at 37° C. for 30 min. The dye was then removed and the cells washed twice with 1 ml PBS per well. The dye was extracted by addition of 500 μl of 50% ethanol and 1% glacial acetic acid in PBS to each well and incubated at room temperature for 15 min with gentle shaking at 120-150 rpm. 100

μl extracted dye from each well was put into 96-well plate and the absorbance at 550 nm was read on an ELISA reader.

Table of Activity Against HSV-1 and HSV-2

| Compound | Treatment | $EC_{50}$ (μg/ml) | $CC_{50}$ (μg/ml) |
| --- | --- | --- | --- |
| SPL-7013 | PT/HSV-2 | 0.61 | >1000 |
| SPL-7013 | PT/HSV-1 | 0.93 | >1000 |
| SPL-7013 | INF/HSV-2 | 3.59 | >1000 |
| SPL-7013 | INF/HSV-1 | 4.59 | >1000 |
| SPL-7304 | PT/HSV-2 | 0.4 | >1000 |
| SPL-7304 | PT/HSV-1 | 3 | >1000 |
| SPL-7304 | INF/HSV-2 | 54.4 | >1000 |
| SPL-7304 | INF/HSV-1 | 50.4 | >1000 |
| SPL-7320 | PT/HSV-2 | 0.6 | >1000 |
| SPL-7320 | PT/HSV-1 | 2.2 | >1000 |
| SPL-7320 | INF/HSV-2 | 33.3 | >1000 |
| SPL-7320 | INF/HSV-1 | 16.4 | >1000 |

PT = Pre-infection treatment
INF = Treatment of infected cells.

(ii) Herpes Virus—2. Efficacy in an Animal Model

The efficacy of SPL-7013 was tested in a genital HSV prevention test in the mouse (strain MS) model. A dose of 15 μl of 100 mg/ml, or 10 mg/ml of the compound was instilled into the vagina of 16 animals 20 sec before HSV-2 infection. SPL-7013 prevented infection and disease in all animals tested compared to controls. Total mortality in three days of the same number of control infected mice was used as an end-point of the tests.

Table of HSV-2 genital tract infection and disease treatment in the mouse

| Concentration (mg/ml) | Number of Animals | Animals Protected Against Disease (%) | Infection (%) |
| --- | --- | --- | --- |
| 100 | 11 | 11/11 (100%) | 11/11 (100% |
| 100 | 12 | 12/12 (100%) | 12/12 (100% |
| 10 | 12 | 11/12 (97%) | 10/12 (83%) |
| PBS control | 12 | 0/12 (0%) | 0/12 (0%) |

All animals treated 20 sec. prior to infection.

C. Human Papillomavirus (HPV). Inhibition of Human Epithelial Cell Uptake.

The compound was evaluated for its ability to inhibit the binding and uptake of human papillomavirus virus-like particles to a human epithelial cell line.

The compound was tested at a range of six dilutions as inhibitor of binding and of uptake of Papillomavirus fluorochrome-tagged Virus-Like-Particles (VLPs) of human papillomavirus type 6b. The VLPs was allowed to bind and to be taken up into the epithelial cells in the presence of SPL-7013. Assay of binding and uptake was determined using flow cytometry and inhibition of binding was reported as a percentage with respect to the binding observed in the absence of inhibitor. The tests were performed in two independent assays Methods Cells. The human epidermoid carcinoma cell line A431 was purchased from the American Type Culture Collection at passage 30 (CRL-1555, Batch F-13530) and maintained in DMEM in 10% FCS.

Human papillomavirus type 6b VLPs were grown and purified according to standard operating procedures. Particles were labelled with a fluorochrome.

The compound was re-dissolved in sterile water to the concentrations of 5 mM and used fresh for the first assay before being frozen at −20° C. It was then thawed for the second assay.

Uptake Assay.

A T75 flask of A431 cells was washed with 10 ml of PBS/EDTA (0.05%) for 5 minutes at 37° C. before being treated with 2 ml trypsin for a further 5 minutes at 37° C. DMEM/10% FCS (10 ml) was added to cells, the cells centrifuged at 1000×g for 5 minutes at RT, and re-suspended in full media at $3 \times 10^5$ cells/ml in a 15 ml tube. Cell were incubated at 37° C. for 2 hours with inversion every 20 minutes so as to allow re-expression of cell surface proteins. Cells were centrifuged at 1000×g for 5 minutes at RT, and re-suspended in serum-free DMEM at $3 \times 10^5$ cells/100 μL and 100 μL of suspension was placed in an 1.5 ml tube. Compound was added to cells at the following six dilutions in 10 μL of PBS: 100 μM, 10 μM, 1.0 μM, 100 nM, 10 nM, 1.0 nM.

Cells were incubated with compound for 30 min at 37° C. before labelled VLPs (200 ng) were added. As a positive control VLPs only, were added to cells and the negative control was cells with VLPs added but incubated on ice. The cells were mixed and incubate at 37° C. for 2 hours. Cells were washed once with 1 ml PBS and fixed in FACS buffer (P13S/4% paraformaldehyde). Analysis was carried out on a Coulter FACS machine.

Analysis.

Results were analysed using WinLisT. Initially forward/side scatter were used to analyse cell size and live cells were gated. The mean fluorescent intensities (MFI) of this gate was generated and used for further analyses. Uptake was reported as the percentage with respect to the binding observed for VLPs alone (100%) verses cells with VLPs incubated on ice (0%).

Results

SPL-7013. Maximal inhibition of uptake (26% uptake) was observed at 1 μM with no further inhibition at higher concentrations. This compound has still shown uptake inhibition at 1 μM and 10 nM. Viral uptake increased after this point with decreasing concentration of SPL-7013.

D. *Chlamydia trachomatis* infection. Efficacy of SPL-7013 in an Animal Model.

Female mice (strain MS) were treated either in the upper or the lower genital tract with a 15 μL instillation of 100 mg/mL solution of SPL-7013, 20 sec prior to infection with *C. trachomatis*. Lower genital tract infection is defined by isolation of the organism by culture from vaginal swab samples collected on days 3 or 6 post challenge. For upper genital tract infection the definition is isolation of the organism by culture from the upper genital tract tissue harvested on day 10 post challenge. Phosphate buffer PBS treated mice were used as controls.

Effects on *C. trachomatis* Genital Tract Infection in Mice Animals Protected Against Infection

| Group | No. animals | Time | Lower Tract (%) | Upper Tract (%) |
| --- | --- | --- | --- | --- |
| Group 1. | | | | |
| SPL-7013 | 16 | −20 sec | 8 (50%)[a] | 8 (50%) |
| PBS | 15 | −20 sec | 1 (7%) | 2 (13%) |
| Group 2. | | | | |
| SPL-7013 | 16 | −20 sec | 6 (38%) | 8 (50%)[a] |
| PBS | 16 | −20 sec | 1 (7%) | 1 (6%) |

Persons skilled in this art will appreciate that variations and modifications may be made to the invention as broadly described herein, other than those specifically described without departing from the spirit and scope of the invention.

It is to be understood that this invention extends to include all such variations and modifications.

REFERENCES

1. Popovic, M.; Sarngadharan, M. G.; Read, E; Gallo, R. C. Detection, isolation, and continuous production of cytopathic retroviruses (HTLV-III) from patients with AIDS and pre-AIDS. *Science* (1984), 224:497-500.
2. Clavel, E; Guyader, M.; Guetard, D.; Salle, M.; Montagnier, L.; Alizon, H. Molecular cloning and polymorphism of the human immunodeficiency virus type 2. *Nature* (1986), 324:691-695.
3. Pauwels, R.; Balzarini, J.; Baba, M.; Snoeck, M. R.; Schols, D.; Herdewijn, R; Desmyter, J, De Clercq, E. Rapid and automated tetrazolium-based colorimetric assay for the detection of anti-HIV compounds. *J. Virol. Methods* (1988), 20:309-321.
4. Clanton et al., *J. AIDS*. (1992), 5:771.

The invention claimed is:
1. A method for the therapeutic treatment of sexually transmitted diseases in a human patient comprising administering topically to the patient an effective amount of a compound of the Formula I:

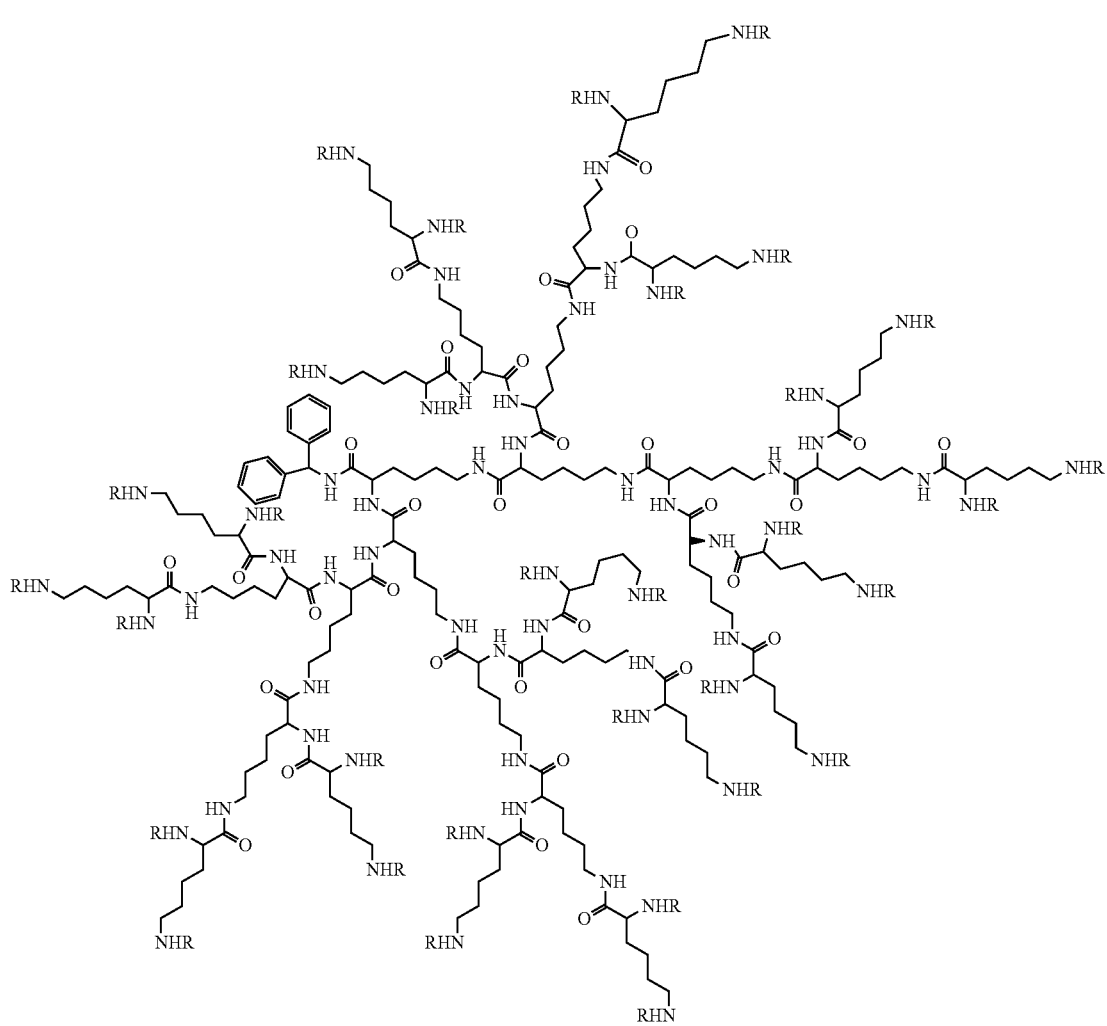

wherein R represents a group of the Formula IV, wherein * indicates the point of attachment:

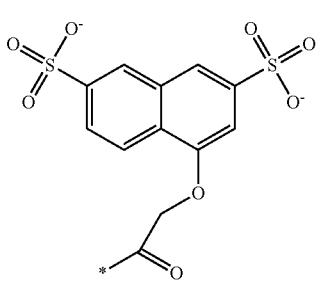

or a pharmaceutically acceptable salt thereof, and wherein said disease is a vaginally or rectally transmitted disease selected from the group consisting of HSV-1, HSV-2, HIV-1, HIV-2, HPV and *Chlamydia trachomatis* infection.

2. The method according to claim 1, wherein the pharmaceutically acceptable salt is selected from metallic salts, organic salts made from organic amines, quaternary amine salts, sulphonium salts, and phosphonium salts.

3. The method according to claim 2, wherein said metallic salt is selected from the group consisting of aluminium, calcium, lithium, magnesium, potassium, sodium, zinc salts.

4. The method according to claim 2, wherein said organic amine is selected from the group consisting of N,N'-dibenzylethylenediamine, chloroprocaine, diethanolamine, ethylenediamine, dicyclohexylamine, meglumine (N-methylglucamine) and procaine.

5. The method according to claim 2, wherein said quaternary amine salt is choline.

* * * * *